United States Patent
Lee et al.

(10) Patent No.: US 7,534,844 B2
(45) Date of Patent: May 19, 2009

(54) MONOMER SUBSTITUTED PHOTOACID GENERATOR OF FLUOROALKYLSULFON AND A POLYMER THEREOF

(75) Inventors: Haiwon Lee, Seongnam-si (KR); Heeyoung Oh, Paju-si (KR); Hyunjin Yoon, Seoul (KR); Yongil Kim, Seoul (KR)

(73) Assignee: IUCF-HYU (Industry-University Cooperation Foundation Hanyang University, Seoul (KR)

( * ) Notice: Subject to any disclaimer, the term of this patent is extended or adjusted under 35 U.S.C. 154(b) by 175 days.

(21) Appl. No.: 11/632,358

(22) PCT Filed: Feb. 16, 2006

(86) PCT No.: PCT/KR2006/000535

§ 371 (c)(1), (2), (4) Date: Jan. 12, 2007

(87) PCT Pub. No.: WO2006/088317

PCT Pub. Date: Aug. 24, 2006

(65) Prior Publication Data

US 2007/0203312 A1  Aug. 30, 2007

(30) Foreign Application Priority Data

Feb. 16, 2005 (KR) .................. 10-2005-0012680

(51) Int. Cl.
*C08F 12/30* (2006.01)
(52) U.S. Cl. .............. 526/243; 526/242; 526/245; 526/287; 526/292.1; 526/292.3; 526/319; 560/221
(58) Field of Classification Search .......... 526/242, 526/286; 560/221
See application file for complete search history.

(56) References Cited

U.S. PATENT DOCUMENTS

| 4,250,053 | A | * | 2/1981 | Smith ................. 502/167 |
| 5,374,697 | A | | 12/1994 | Muller |
| 6,111,143 | A | | 8/2000 | Park et al. |
| 2002/0182541 | A1 | * | 12/2002 | Gonsalves ............ 430/287.1 |
| 2005/0018595 | A1 | * | 1/2005 | Conroy et al. ............ 369/288 |

OTHER PUBLICATIONS

Maoz, Rivka et al.: "Constructive Nanolithography: Site-Defined Silver Self-Assembly on Nanoelectrochemically Patterned Monolayer Templates", *Adv. Mater.* 2000, vol. 12, No. 6, pp. 424-429.

Sugimura, Hiroyuki et al.: "Scanning probe anodization: Nanolithography using thin films of anodically oxidizable materials as resists", *J. Vac. Sci. Technol. A*, vol. 14, No. 3, May/Jun. 1996, pp. 1223-1227.

Birkelund, K. et al.: "New approaches to atomic force microscope lithography on silicon", *J. Vac. Sci. Technol. B*, vol. 15, No. 6, Nov./Dec. 1997, pp. 2912-2915.

(Continued)

*Primary Examiner*—Marc S. Zimmer
*Assistant Examiner*—Nicole M Buie
(74) *Attorney, Agent, or Firm*—Frommer Lawrence & Haug LLP; Ronald R. Santucci

(57) ABSTRACT

The present invention relates to a novel compound with a fluoroalkylsulfonium photoacid generating group and novel copolymers having superior solubility in organic solvents, which is prepared from radical polymerization of the novel compound with methacrylate monomers.

6 Claims, 4 Drawing Sheets

OTHER PUBLICATIONS

Avouris, Phaedon et al.: "Atomic force microscope tip-induced local oxidation of silicon: kinetics, mechanism, and nanofabrication", *Appl. Phys. Lett*, vol. 71, No. 2, Jul. 14, 1997, pp. 285-287.

Asakura, Toshikage et al.: "Novel Photoacid Generators", *Journal of Photopolymer Science and Technology*, vol. 13, No. 2 (2000), pp. 223-230.

Kim, Jinchul et al.: "Nanometer-Scale Lithography of the Ultrathin Films with Atomic Force Microscope" 13 pages.

Kim, Jinchul et al.: "Atomic Force Microscope Based Nanolithography of Self-Assembled Organosilane Monolayer Resists", 13 pages.

* cited by examiner

[Fig. 1]
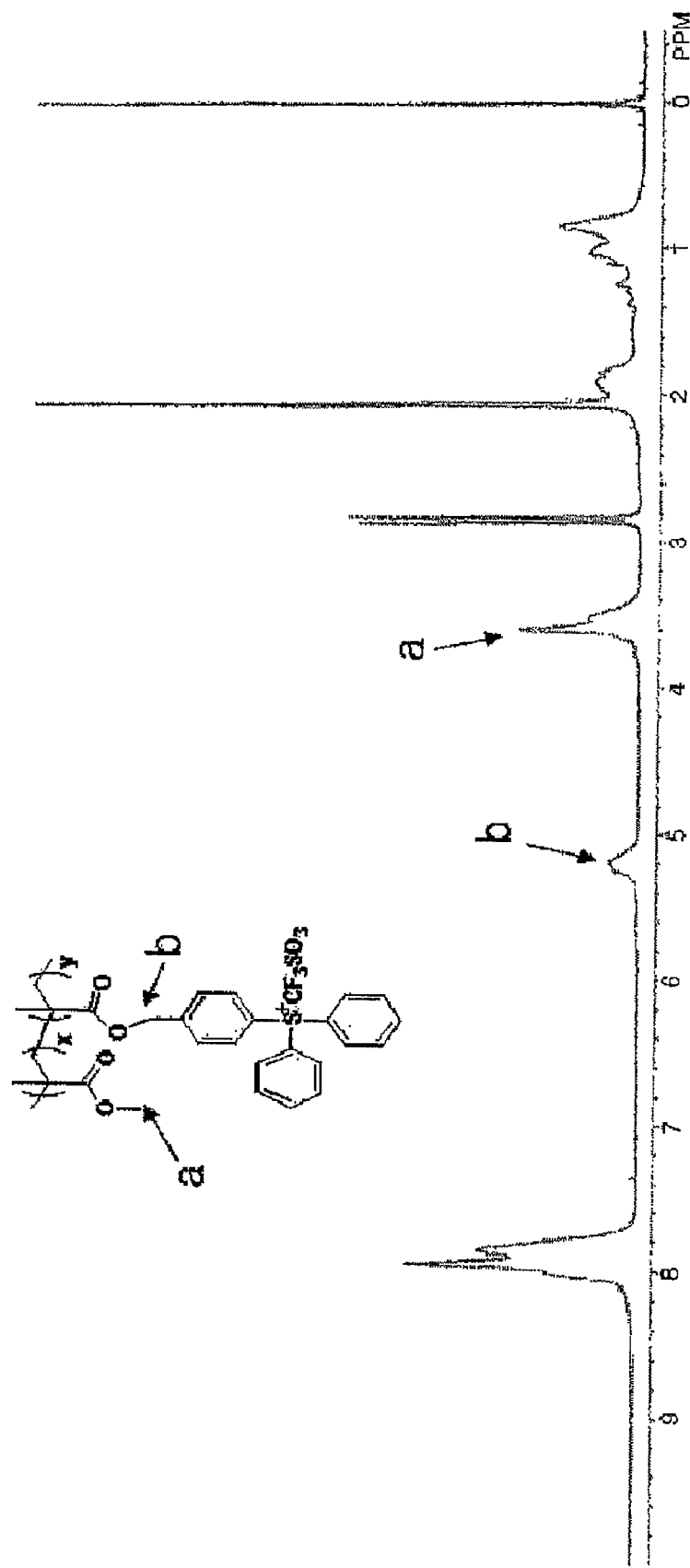

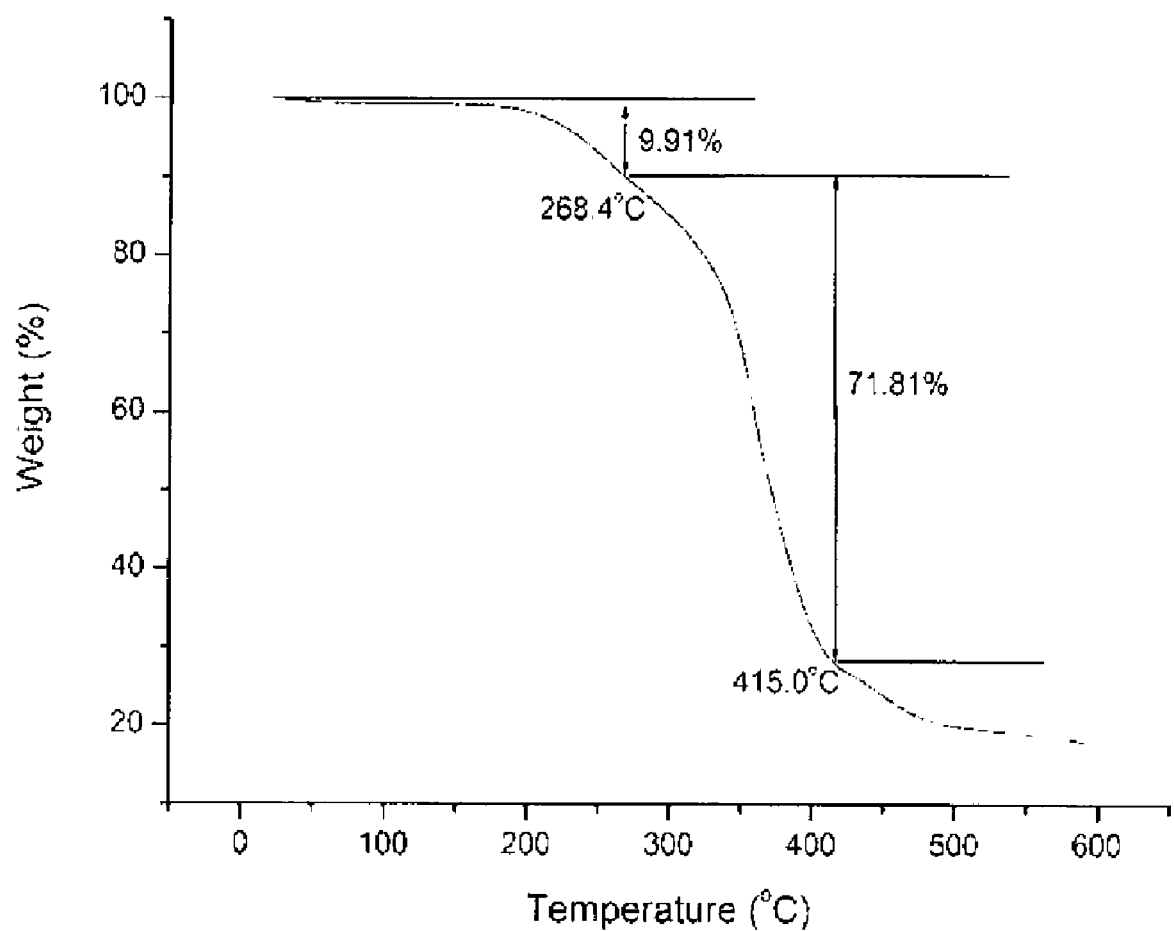
[Fig. 2]

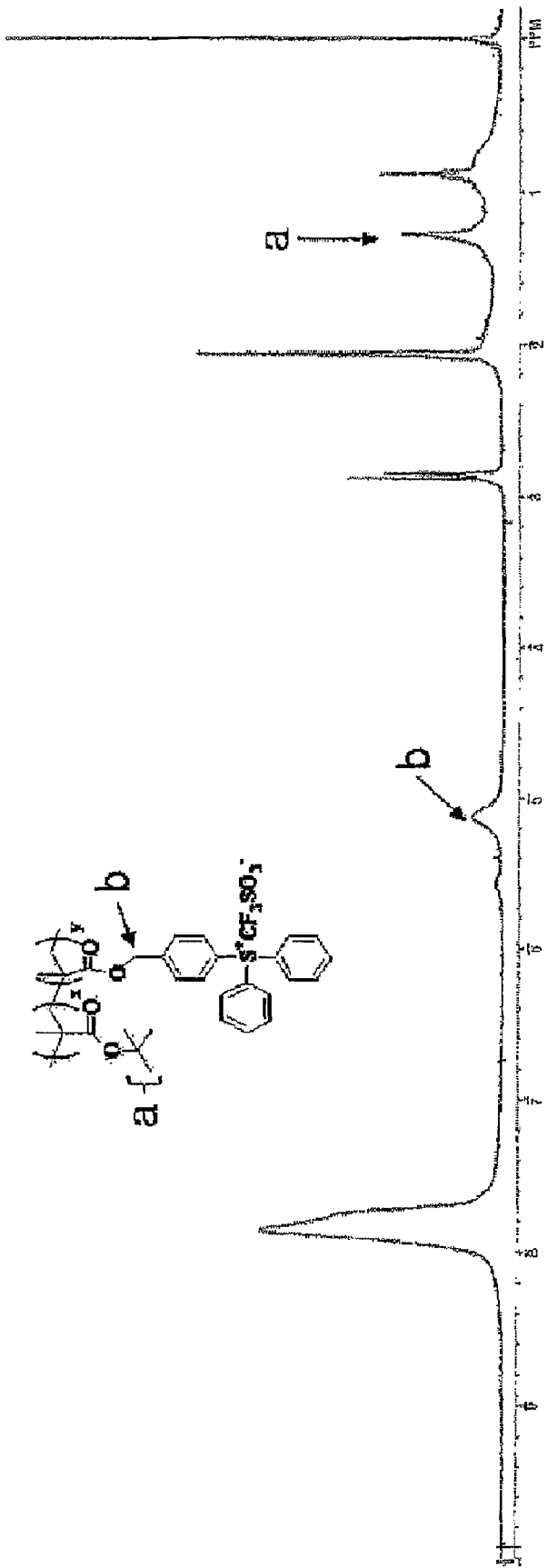
[Fig. 3]

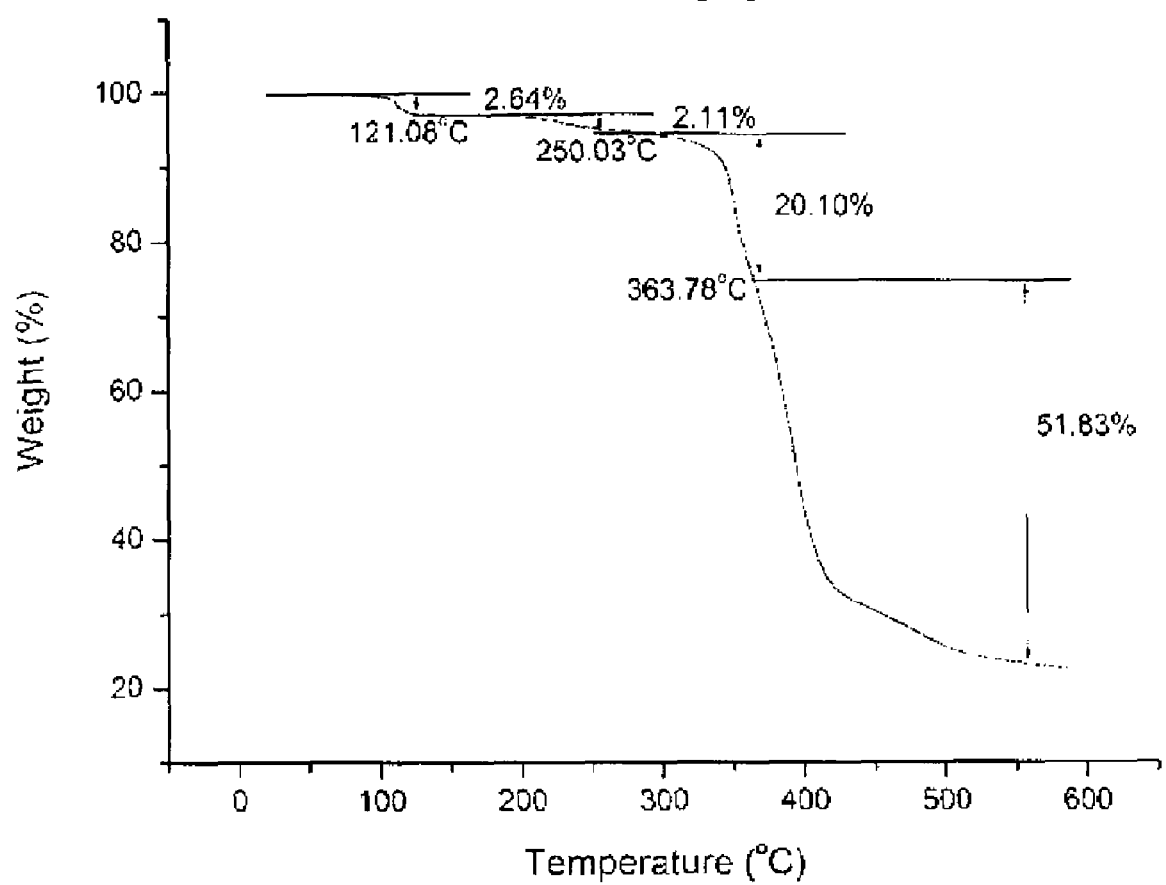
[Fig. 4]

MONOMER SUBSTITUTED PHOTOACID GENERATOR OF FLUOROALKYLSULFON AND A POLYMER THEREOF

This application is a 371 of PCT/KR2006/000535 filed on Feb. 16, 2006, published on August 24, 2006 under publication number WO 2006/088317 A1 which claims priority benefits from Korean Patent Application No. 10-2005-0012680 filed Feb. 16, 2005.

TECHNICAL FIELD

The present invention relates to a novel compound with a fluoroalkylsulfonium-substituted photoacid generating group and a novel copolymer with superior solubility in organic solvents which is prepared from radical polymerization of the novel compound with methacrylate monomers.

BACKGROUND ART

In conventional AFM lithography, a pattern formation is mostly performed by preparing self-assembled monolayers using an organic resist [*Jpn. J. Appl. Phys.*, 37, 7148, 1998, Kim J. C., *J. Kor. Phys. Soc.*, 35, 1013, 1999, Kim, J. C., *Adv. Mater.*, 12, 6, 424, 2000, Rivka M.].

The process of oxide pattern formation by AFM is as follows. An organic thin film is formed on a silicon substrate with a predetermined thickness. Then, a voltage in the order of several volts is applied locally using an AFM tip to form an oxide pattern. The resultant silicon oxide is etched much faster than other parts because it has a loose structure. The part of the organic thin film to which the voltage has not been applied can be used as a resist during etching to obtain a wanted positive pattern. However, in practice, it is difficult to completely remove the thin film after pattern formation because of its strong chemical bonding with the substrate.

In AFM lithography, applied voltage, electric current, scanning rate, humidity, capacity of resist, etc., are important factors [*Vac. Sci. Technol.*, 1223, 1996, Sugimura, A., *J. Vac. Sci. Technol.*, 2912, 1997, Birkelund K., *J. Appl. Phys. Lett.*, 285, 1997, Avouris P.].

Unless lithography is performed under optimum conditions, patterns with irregular linewidth and broken lines are obtained. For better pattern formation, the development of high performance resist is required and such conditions as applied voltage, scanning rate and humidity should be appropriately controlled.

Sulfonium is usually used as a photoacid initiator or radical photoinitiator in polymerization or as an acid catalyst generator to deprotect organic compounds. A variety of uses have been developed for sulfonium, which generates cation photoacid initiators when excited by UV in the specific region. And, with the recent development in electronics, it is used for micropattern formation in microelectronics. The sulfonium cation photoinitiator has good photopolymerization efficiency as it produces strong acid when exposed to light, but is disadvantageous in that it is less soluble in organic solvents.

With regard to this problem, there is a report that the use of non-ionic photoinitiators generating acids by exposure to light improves solubility in organic solvents [*Journal of Photopolymer Science and Technology*, Vol. 13, No. 2(2000), pp 223-230]. However, the acids generated by the non-ionic photoinitiators are weak acids such as methylsulfonic acid, propylsulfonic acid and camphosulfonic acid, not the strong trifluoromethanesulfonic acid.

DISCLOSURE OF THE INVENTION

The present inventors have made numerous efforts to solve the problems of low solubility of sulfonium salts in organic solvents and nonuniformity and discontinuity of linewidth during oxide pattern formation. In doing so, they found out that a novel copolymer prepared from radical polymerization of a novel compound, which is prepared by substituting diphenyl sulfoxide with a novel fluoroalkylsulfonium salt, and methylmethacrylate monomers has good solubility in organic solvents.

Thus, it is an object of the present invention to provide a novel compound substituted with fluoroalkylsulfonium.

It is another object of the present invention to provide a novel copolymer in which a fluoroalkylsulfonium photoacid generating group is introduced at the side chain.

The present invention relates to a compound substituted with fluoroalkylsulfonium, which is represented by the formula 1 below:

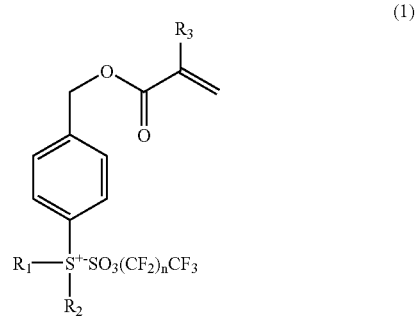

(1)

where $R_1$ and $R_2$ are independently a phenyl substituted with an electron donating group or an electron withdrawing group selected from the group consisting of $C_1$-$C_6$ alkylcarbonyl, aldehyde, cyano, nitro and phenyl;

$R_3$ is a hydrogen atom or a linear, branched or cyclic $C_1$-$C_6$ alkyl group; and n is an integer of from 0 to 20.

The present invention also relates to a copolymer represented by the formula 2, wherein a fluoroalkylsulfonium photoacid generating group is introduced at the side chain:

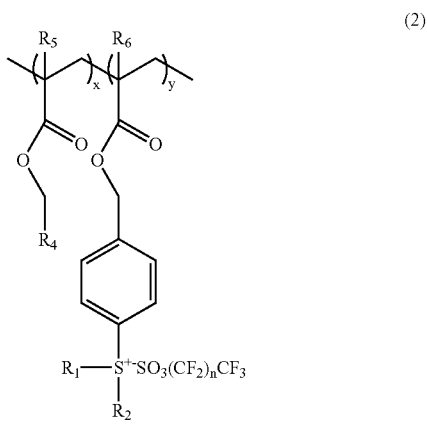

(2)

wherein

R₁ and R₂ are the same as defined in the formula 1;

R₄ is a linear, branched or cyclic $C_1$-$C_{20}$ alkyl group;

R₅ and R₆ are independently a hydrogen atom or a linear, branched or cyclic $C_1$-$C_6$ alkyl group;

n is an integer of from 0 to 20; and x+y=1, where $0 \leqq x \leqq 0.99$ and $0.01 \leqq y \leqq 1$.

Hereunder is given a more detailed description of the present invention.

The present invention relates to a novel monomer represented by the formula 1, which has a fluoroalkylsulfonium photoacid generating group.

The compound represented by the formula 1 generates cation initiators when exposed to a UV light in a specific region, and thus is used, for example, as a photoacid initiator, radical initiator and acid catalyst generator in the deprotection of organic compounds.

The preparation method of the compound represented by the formula 1 in accordance with the present invention comprises the steps of:

(a) synthesis of alkylsulfonium trifluorate from diphenyl sulfoxide;

(b) synthesis of halogen-substituted alkylsulfonium trifluorate; and (c) synthesis of alkylacryloyloxy alkylsulfonium trifluorate.

The three synthesis steps of preparing the fluoroalkylsulfonium-substituted compound are described in more detail.

First, diphenyl sulfoxide and toluene are dissolved in methylene chloride and the temperature inside the reactor is adjusted to −78° C. using acetone-dry ice. Then, trifluoric anhydride is slowly added dropwise. After 1-2 hours of reaction at −78° C., the reaction solution is slowly heated to room temperature and is washed with saturated sodium bicarbonate solution and distilled water. After the solution is dried with anhydrous magnesium sulfate, the solvent is removed under reduced pressure. Then, recrystallization is carried out after dissolving the resultant in hot ethyl acetate of about 60-70° C. to obtain alkylsulfonium trifluorate.

Next, the obtained alkylsulfonium trifluorate is reacted with halosuccinimide to obtain halogen-substituted alkylsulfonium trifluorate. In the reaction, a small amount of benzoyl peroxide is used as a reaction initiator. The solvents are used without further purification in the reaction. For the solvent, a mixture of carbon disulfide, carbon tetrachloride and dichloromethane can be used, preferably in the mixing proportion of 1-100:1-100:1-100 based on weight. Preferably, the reaction is performed for 10-12 days.

Next, the obtained halogen-substituted alkylsulfonium trifluorate is reacted with sodium methacrylate, sodium iodide, tetraammonium bromide and dihydroxyquinone to obtain alkylacryloyloxy alkylsulfonium trifluorate. Preferably, the reaction is performed for about 1-2 hours and acetonitrile is used as a solvent without further purification.

The present invention is also characterized by a novel copolymer represented by the formula 2 in which a fluoroalkylsulfonium photoacid generating group is introduced at the side chain.

The novel copolymer represented by the formula 2, in which a fluoroalkylsulfonium photoacid generating group is introduced at the side chain, is prepared from radical polymerization of the fluoroalkylsulfonium compound represented by the formula 1 with methacrylate monomers. In the radical polymerization, a small amount of a common radical initiator, for example, azobisisobutyronitrile, etc., is added.

The obtained copolymer represented by the formula 2, in which a fluoroalkylsulfonium photoacid generating group is introduced at the side chain, has improved solubility in organic solvents and superior photopolymerization ability thanks to the substituted photoacid generating group.

BRIEF DESCRIPTION OF THE DRAWINGS

FIG. 1 shows a result of ¹H-NMR (nuclear magnetic resonance) analysis of the copolymer of the present invention prepared in Example 2.

FIG. 2 shows a result of TGA (thermal gravimetric analysis) analysis of the copolymer of the present invention prepared in Example 2.

FIG. 3 shows a result of ¹H-NMR (nuclear magnetic resonance) analysis of the copolymer of the present invention prepared in Example 3.

FIG. 4 shows a result of TGA (thermal gravimetric analysis) analysis of the copolymer of the present invention prepared in Example 3.

BEST MODE FOR CARRYING OUT THE INVENTION

Hereinafter, the present invention is described in further detail through examples. However, the following examples are only for the understanding of the present invention and they should not be construed as limiting the scope of the present invention.

EXAMPLE 1

Synthesis of Monomer Substituted with a Photoacid Generating Group

The following scheme 1 illustrates synthesis of 4-methacryloyloxyphenyl diphenylsulfonium trifluorate, in which a novel photoacid generating group is substituted, but the present invention is not limited to this example.

[Scheme 1]

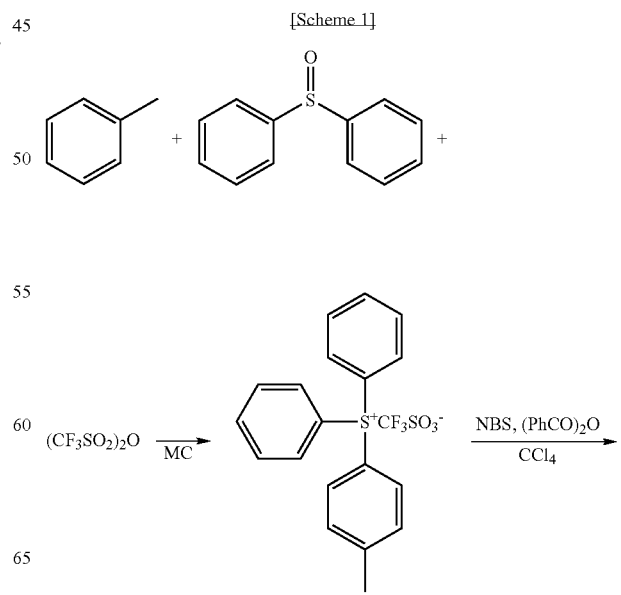

-continued

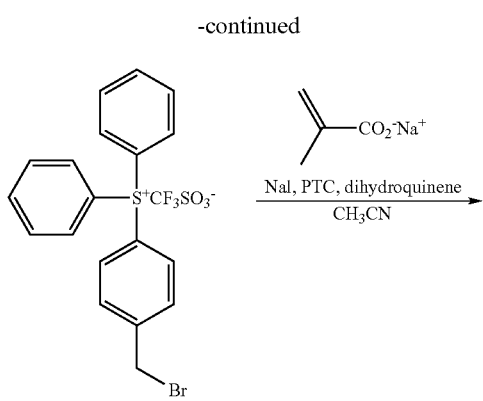

(1) Synthesis of 4-methylphenyl diphenylsulfonium trifluorate 10 g of diphenyl sulfoxide (49.4 mmol) and 5.1 g of toluene (49.4 mmol) were dissolved in 500 mL of dichloromethane. Temperature of reactor containing the solution was adjusted to about −78° C. using an acetone-dry ice bath and 14.8 g of trifluoric anhydride (49.4 mmol) was slowly added dropwise. Then, the solution was stirred at the same temperature for 1 hour and slowly heated to room temperature. After 30 minutes of stirring, the reaction solution washed with saturated sodium bicarbonate solution and then with distilled water. After the solution was dried with anhydrous magnesium sulfate, the solvent was removed by using a rotary evaporator and the residue was recrystallized in hot ethyl acetate to obtain 4-methylphenyl diphenylsulfonium trifluorate (yield=50%).

Structure of thus obtained compound was confirmed by $^1$H-NMR and $^{19}$F-NMR spectroscopy.

$^1$H-NMR (CDCl$_3$, ppm): 2.48(s, 3H), 7.46(d, 2H phenyl), 7.60(d, 2H phenyl), 7.70(m, 10H phenyl)

(2) Synthesis of 4-bromomethylphenyl diphenylsulfonium trifluorate 5 g (11.7 mmol) of the sulfonium compound synthesized in (1) was mixed with 5.5 g (30.9 mmol) of N-bromosuccinimide and dissolved in a mixture solvent (30 mL carbon disulfide, 30 mL carbon tetrachloride, 40 mL dichloromethane). After 0.3 g (1.2 mmol) of benzoyl peroxide was added to the mixture, the mixture was stirred for 10 days under heat reflux. The solvent was removed from the reaction solution under reduced pressure and the residue was dissolved in 100 mL of dichloromethane, washed twice with distilled water and dried with anhydrous magnesium sulfate. Then, the solvent was removed with a rotary evaporator and purification was performed by column chromatography to obtain 4-bromomethylphenyl diphenylsulfonium trifluorate (yield=60%).

Structure of thus obtained compound was confirmed by $^1$H-NMR spectroscopy.

$^1$H-NMR (CDCl$_3$, ppm): 4.51(s, 2H), 7.30(m, 14H phenyl)

(3) Synthesis of 4-methacryloyloxyphenyl diphenylsulfonium trifluorate 22 g (3.9 mmol) of the compound synthesized in (2), 0.47 g (4.3 mmol) of sodium methacrylate, 60 mg (0.4 mmol) of sodium iodide, 84 mg (0.4 mmol) of tetraethylammonium bromide and a trace of dihydroxyquinone were dissolved in 20 mL of acetonitrile and the mixture was stirred for 1.5 hours under heat reflux. The solvent was removed from the reaction solution under reduced pressure and the residue was dissolved in 30 mL of distilled water. The product was extracted with dichloromethane and the solution was dried with anhydrous magnesium sulfate. Then, the solvent was removed with a rotary evaporator and purification was performed by column chromatography to obtain 4-methacryloyloxyphenyl diphenylsulfonium trifluorate (yield=93%).

Structure of thus obtained compound was confirmed by $^1$H-NMR spectroscopy.

$^1$H-NMR (CDCl$_3$, ppm): 1.97(s, 1H, C—CH$_3$), 5.28(2H, O—CH$_3$), 5.64(1H, CH$_2$=), 6.66(1H, CH$_2$=), 7.70(14H, phenyl)

EXAMPLE 2

Synthesis of Copolymer with a Photoacid Generating Group Introduced at Side Chain The following scheme 2 illustrates synthesis of poly(methylmethacrylate-co-4-diphenylsulfoniumtrifluorate-benzylmethacrylate) as an example of a copolymer in which a photoacid generating group is substituted at the side chain, but the present invention is not limited to this example.

[Scheme 2]

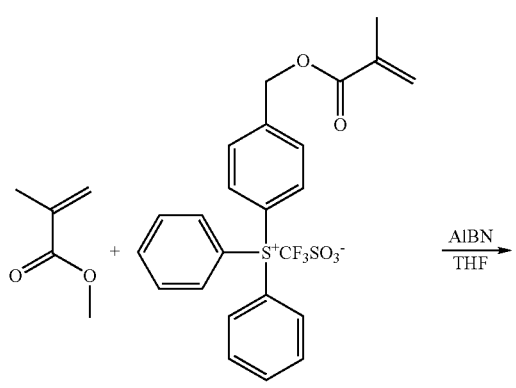

-continued

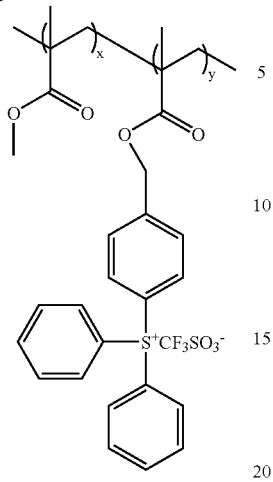

1.35 g (13.5 mmol) of methylmethacrylate and 3.45 g (6.75 mmol) of the compound synthesized in Example 1 were dissolved in 300 mL of purified tetrahydrofuran. After adding 22 mg (0.27 mmol) of azobisisobutyronitrile, the mixture was stirred for 24 hours under heat reflux. The reaction solution was slowly poured into a 7:3 mixture solution of isopropyl and n-hexane for precipitation. The precipitate was filtered and dried in vacuum to obtain a compound represented by the formula 2 (yield=50%).

$^1$H-NMR and TGA analysis results of thus obtained compound are shown in FIG. 1 and FIG. 2.

According to the $^1$H-NMR analysis, the ratio of x to y was 1.92:1 and the weight average molecular weight was about 4500.

EXAMPLE 3

A copolymer represented by the formula 2 was synthesized in the same manner as in Example 2, except that tert-butylmethacrylate and the compound synthesized in Example 1 were used with 1:1 molar ratio (yield=50%).

$^1$H-NMR and TGA analysis results of thus obtained compound are shown in FIG. 3 and FIG. 4.

According to the $^1$H-NMR analysis, the ratio of x to y was 1:1 and the weight average molecular weight was about 5000.

EXAMPLE 4

A copolymer represented by the formula 2 was synthesized in the same manner as in Example 2, except that tetrahydropyranylmethacrylate and the compound synthesized in Example 1 were used with 1:1 molar ratio (yield=45%).

$^1$H-NMR and TGA analysis results of thus obtained compound are shown in FIG. 3 and FIG. 4.

According to the $^1$H-NMR analysis, the ratio of x to y was 1:1 and the weight average molecular weight was about 5000.

The synthesized copolymers represented by the formula 2 showed good solubility in a variety of solvents, including acetone, methylene chloride, chloroform, methanol, ethanol, isopropyl alcohol, dimethylsulfoxide and tetrahydrofuran.

INDUSTRIAL APPLICABILITY

As apparent from the above description, the copolymer of the present invention, which is polymerized from a novel monomer with a fluoroalkylsulfonium photoacid generating group, has good solubility in organic solvents and superior coating ability.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A compound substitute with fluoroalkylsulfonium, which is represented by the following formula 1:

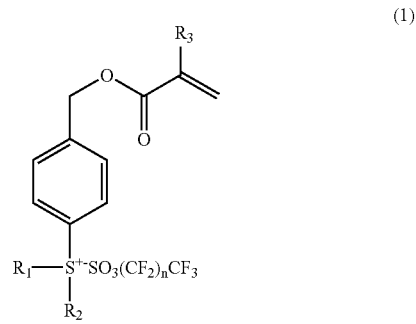

wherein $R_1$ and $R_2$ are independently an unsubstituted phenyl or a phenyl substituted with an electron donating group or an electron withdrawing group selected from the group consisting of $C_1$-$C_6$ alkylcarbonyl, aldehyde, cyano, nitro and phenyl;

$R_3$ is a hydrogen atom or a linear, branched or cyclic $C_1$-$C_6$ alkyl group, and n is an integer of from 0 to 20.

2. A copolymer in which a fluoroalkylsulfonium substituted photoacid generating group is introduced at the side chain, which is represented by the following formula 2:

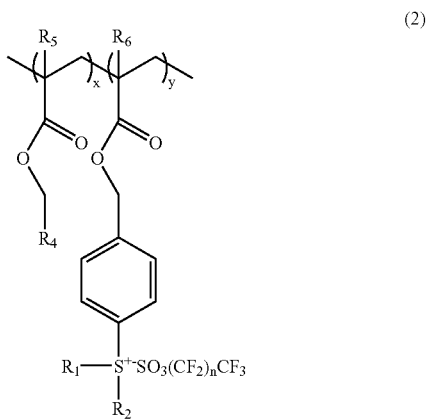

wherein $R_1$ and $R_2$ are independently an unsubstituted phenyl or a phenyl substituted with an electron donating group or an electron withdrawing group selected from the group consisting of $C_1$-$C_6$ alkylcarbonyl, aldehyde, cyano, nitro and phenyl;

$R_4$ is a linear, branched or cyclic $C_1$-$C_{20}$ alkyl group;

$R_5$ and $R_6$ are independently a hydrogen atom or a linear, branched or cyclic $C_1$-$C_6$ alkyl group;

n is an integer of from 0 to 20; and x+y=1, where $0 \leqq x \leqq 0.99$ and $0.01 \leqq y \leqq 1$.

3. The compound of claim 1, wherein $R_1$ and $R_2$ are independently an unsubstituted phenyl and n is 0.

4. The compound of claim 3, wherein $R_3$ are methyl.

5. The copolymer of claim 1, wherein $R_1$ and $R_2$ are independently an unsubstituted phenyl and n is 0.

6. The copolymer of claim 5, wherein $R_4$, $R_5$ and $R_6$ are methyl.

* * * * *